US008563839B2

(12) United States Patent
Scheer et al.

(10) Patent No.: US 8,563,839 B2
(45) Date of Patent: Oct. 22, 2013

(54) METHODS OF REDUCING LEAF SENESCENCE USING METHYL DIHYDROJASMONATE

(75) Inventors: Barbara Scheer, San Francisco, CA (US); Justin Scheer, San Francisco, CA (US)

(73) Assignee: New Biology, Inc., Burlingame, CA (US)

( * ) Notice: Subject to any disclaimer, the term of this patent is extended or adjusted under 35 U.S.C. 154(b) by 28 days.

(21) Appl. No.: 13/196,755

(22) Filed: Aug. 2, 2011

(65) Prior Publication Data

US 2011/0287938 A1    Nov. 24, 2011

Related U.S. Application Data

(63) Continuation-in-part of application No. 12/424,790, filed on Apr. 16, 2009, now Pat. No. 8,013,226.

(60) Provisional application No. 61/050,676, filed on May 6, 2008.

(51) Int. Cl.
A01H 5/00    (2006.01)

(52) U.S. Cl.
USPC ........................................ 800/323; 504/116.1

(58) Field of Classification Search
USPC ........................................ 800/323; 504/116.1
See application file for complete search history.

(56) References Cited

U.S. PATENT DOCUMENTS

| | | | |
|---|---|---|---|
| 5,304,529 A | 4/1994 | Yokoyama et al. | |
| 5,378,819 A | 1/1995 | Ryan et al. | |
| 5,639,794 A | 6/1997 | Emerson et al. | |
| 5,776,860 A | 7/1998 | Kamuro et al. | |
| 5,814,581 A * | 9/1998 | Hirakawa et al. | 504/140 |
| 5,888,501 A | 3/1999 | Backman et al. | |
| 5,935,809 A | 8/1999 | Ryan, Jr. et al. | |
| 6,174,840 B1 | 1/2001 | Pauson et al. | |
| 6,299,926 B1 | 10/2001 | Balakrishnan et al. | |
| 6,387,847 B1 | 5/2002 | Yvin et al. | |
| 6,524,998 B1 | 2/2003 | Kloepper et al. | |
| 6,544,499 B1 | 4/2003 | Glenn et al. | |
| 6,649,566 B2 | 11/2003 | Doostdar | |
| 6,743,752 B2 | 6/2004 | Dutcheshen | |
| 6,890,525 B2 | 5/2005 | Hick et al. | |
| 7,176,163 B1 | 2/2007 | Takahashi et al. | |
| 7,297,659 B2 | 11/2007 | Nautiyal et al. | |
| 7,541,155 B2 | 6/2009 | Enan | |
| 7,820,153 B2 | 10/2010 | Hick et al. | |
| 8,115,053 B2 | 2/2012 | Roberts et al. | |
| 2002/0035738 A1 | 3/2002 | Thomma et al. | |
| 2002/0099101 A1 | 7/2002 | Emerson et al. | |
| 2003/0005484 A1 | 1/2003 | Crandall, Jr. et al. | |
| 2004/0033902 A1 | 2/2004 | Haddad | |
| 2004/0175439 A1 | 9/2004 | Cyr | |
| 2006/0165818 A1 | 7/2006 | Hysmith | |
| 2006/0178270 A1 | 8/2006 | Chevolot et al. | |
| 2009/0082453 A1 | 3/2009 | Scheer et al. | |
| 2012/0077674 A1 | 3/2012 | Cargeeg et al. | |

FOREIGN PATENT DOCUMENTS

| | | |
|---|---|---|
| EP | 0445867 A1 | 9/1991 |
| EP | 0912096 A2 | 5/1999 |
| EP | 1038965 A1 | 9/2000 |
| EP | 1321472 A2 | 6/2003 |
| JP | 2002047104 | 2/2002 |
| WO | 9847375 | 10/1998 |
| WO | 2005102047 A1 | 11/2005 |
| WO | 2006054907 A1 | 5/2006 |

OTHER PUBLICATIONS

Belhadj et al. "Methyl jasmonate Induces Defense Responses in Grapevine and Triggers Protection against *Erysiphe* necator," Journal of Agricultural and Food Chemistry (2006) 54, pp. 9119-9125.*
Darras et al. "Acibenzolar-S-methyl and methyl jasmonate treatments of glasshouse-grown freesias suppress post-harvest petal specking caused by *Botrytis cinerea*," Journal of Horticultural Science & Biotechnology (2006) 81 (6) pp. 1043-1051.*
Aerts, R. et al., "Methyl Jasmonate Vapor Increases the Developmentally Controlled Synthesis of Alkaloids in *Catharantus* and *Cinchona* Seedlings," The Plant Journal, vol. 5, No. 5, pp. 635-643, 1994.
Baldwin, I. et al. "Effects of Octadecanoid Metabolites and Inhibitors on Induced Nicotine Accumulation in *Nicotiana sylvestris*," Journal of Chemical Ecology, vol. 22, No. 1, pp. 61-74, 1996.
Belhadj, A. et al. "Methyl Jasmonate Induces Defense Responses in Grapevine and Triggers Protection Against *Erysiphe* Necator," Journal of Agricultural and Food Chemistry, vol. 54, pp. 9119-9125, 2006.
Blechert, S. et al. "The Octadecanoic Pathway: Signal Molecules for the Regulation of Secondary Pathways", Proceedings of the National Academy of Sciences, vol. 92, pp. 4099-4105, 1995.
Chen, H. et al. "Constitutive Activation of the Jasmonate Signaling Pathway Enhances the Production of Secondary Metabolites in Tomat," FEBS Letters, vol. 580, pp. 2540-2546, 2006.
Chou, C. et al. "Methyl Jasmonate, Calcium, and Leaf Senescence in Rice," Plant Physiology, vol. 99, pp. 1693-1694, 1992.
Capiati, D., et al "Wounding increases salt tolerance in tomate plants: evidence on the participation of calmodulin-like activities in cross-tolerance signalling." Journal of Experimental Botany, vol. 57, No. 10, pp. 2391-2400, 2006.
Dihn, S. et al. "Effects of Combined Methyl Jasmonate and Ethylene-Inhibitor Treatments against *Botrytis cinerea* Infecting Geraldton Waxflower," Acta Horticulturae (International Society for Horticultural Science), vol. 755, pp. 527-532, 2007.
Darras, A. et al. "Acibenzolar-S-methyl and Methyl Jasmonate Treatments of Glasshouse-grown Freesias Suppress Post-harvest Petal Specking Caused by *Botrytis cinerea*," Journal of Horticultural Science & Biotechnology, vol. 81, No. 6, pp. 1043-1051, 2006.

(Continued)

Primary Examiner — Susan McCormick Ewoldt
(74) Attorney, Agent, or Firm — PatentBest; Andrew McAleavey

(57) ABSTRACT

Methods for reducing leaf senescence in plants or plant portions by treating them with methyl dihydrojasmonate are disclosed. The methyl dihydrojasmonate may be in the form of an aqueous foliar spray, which may also include additives such as wetting agents, adjuvants, emulsifiers, dispersants, spreaders, surfactants, anchorage, disintegrants, and plant nutrients.

19 Claims, No Drawings

(56) References Cited

OTHER PUBLICATIONS

Darras et al., "Methyl Jasmonate Vapour Treatment Suppresses Speckling Caused by *Botrytis cinerea* on cut *Freesia* hybrida L. Flowers," Postharvest Biology and Technology, vol. 38, No. 2, pp. 175-182, Nov. 2005.

Del Amor, F., et al "Alleviation of salinity stress in broccoli using foliar urea or methyl-jasmonate: analysis of growth, gas exchange, and isotope composition." Plant Growth Regulation, pp. 1-8-8, 2010.

Gapper, N. et al. "Novel jasmonate amino acid conjugates in *Asparagus officinalis* during harvest-induced and natural foliar senescence," Physiologia Plantarum, vol. 114, pp. 116-124, 2002.

Gast, K. "Methyl Jasmonate and Long Term Storage of Fresh Cut Peony Flowers," International Society for Horticultural Science Acta Horticulturae 543: VII International Symposium on Postharvest Physiology of Ornamental Plants, pp. 327-330, 2001.

Glick, A. et al. "Methyl Jasmonate Enhances Color and Carotenoid Content of Yellow-Pigmented Cut Rose Flowers," Acta Horticulturae (International Society for Horticultural Science), vol. 755, pp. 243-250, 2007.

Gundlach, H. et al. "Biological Activity and Biosynthesis of Pentacyclic Oxylipins: The Linoleic Acid Pathway," Phytochemistry, vol. 47, No. 4, pp. 527-537, 1998.

Guranowski, A., et al "Substrate specificity and products of side-reactions catalyzed by jasmonate: amino acid synthetase (JAR1)." FEBS Letters 581, pp. 815-820, 2007.

Hamilton, E., et al "Heart-Shock Proteins Are Induced in Unstressed Leaves of *Nicotiana attenuata* (Solanaceae) When Distant Leaves Are Stressed." American Journal of Botany, vol. 88, No. 5, pp. 950-955, 2001.

Hassanein, R., et al "Role of Jasmonate Acid and Abscisic Acid Treatments in Alleviating the Adverse Effects of Drought Stress and Regulating Trypsin Inhibitor Production in Soybean Plant." Australia Journal of Basic and Applied Sciences, vol. 3, No. 2, pp. 904-919, 2009.

He, Y. et al. "Evidence Supporting a Role of Jasmonic Acid in *Arabidopsis* Leaf Senescence," Plant Physiology, vol. 128, pp. 876-884, 2002.

Hijwegen, T. et al. "Resistance to *Sphaerotheca* Pannosa in Roses Induced by 2,6-dichloroisonicotinic Acid," Plant Pathology, vol. 45, pp. 631-635, 1996.

Hudgins, J. et al. "Responsible for Conifer Phloem Defense Responses and Reprogramming of Stem Cambial Zone for Traumatic Resin Duct Formation," Plant Physiology Preview, vol. 135, pp. 2134-2149, Aug. 2004.

Ishikawa, A. et al. "Jasmonate-Inducible Expression of a Potato Cathepsin D Inhibitor-GUS Gene Fusion in Tobacco Cells," Plant Molecular Biology, vol. 26, pp. 403-414, 1994.

Ishikawa, A. et al. "Structure-Activity Relationships of Jasmonates in the Induction of Expression of Two Proteinase Inhibitor Genes of Potato," Bioscience, Biotechnology, and Biochemistry, vol. 58, No. 3, pp. 544-547, 1994.

Jones, J. et al. "The Plant Immune System," Nature, vol. 444, pp. 323-329, Nov. 16, 2006.

Kappers, I., et al "Genetic Variation in Jasmonic Acid- and Spider Mite-Induced Plant Volatile Emission of Cucumber Accessions and Attraction of the Predator *Phytoseiulus persimilis*." Journal of Chemical Ecology, vol. 36, pp. 500-512, 2010.

Keeling, C., et al "Genes, enzymes and chemicals of terpenoid diversity in the constitutive and induced defence of conifers against insects and pathogens," New Phytologist, vol. 170, pp. 657-675, 2006.

Malkawi, A. et al. "Plant Hormones Isolated from "Katandin" Potato Plant Tissues and the Influence of Photoperiod and Temperature on Their Levels in Relation to Tuber Induction," Journal of Plant Growth Regulation, vol. 26, No. 4, pp. 308-317, 2007.

Martin, D., et al "Induction of Volatile Terpene Biosynthesis and Diurnal Emission by Methyl Jasmonate in Foliage of Norway Spruce." Plant Physiology, vol. 132, pp. 1586-1599, 2003.

Meir, S. et al. "Use of Methyl Jasmonate for Suppression of Botrytis Rot in Various Cultivars of Cut Rose Flowers" International Society for Horticultural Science Acta Horticulturae 669: VIII International Symposium on Postharvest Physiology of Ornamental Plants, pp. 91-98, 2005.

Meir, S. et al. "Suppression of Botrytis Rot in Cut Rose Flowers by Postharvest Application of Methyl Jasmonate," Postharvest Biology and Technology, vol. 13, pp. 235-243, 1998.

Miersch, O. et al. "Structure-Activity Relations of Substituted, Deleted or Stereospecifically Altered Jasmonic Acid in Gene Expression of Barley Leaves," Phytochemistry, vol. 50, pp. 353-361, 1999.

Mithofer, A. et al. "Structural and Biologial Diversity of Cyclic Octadecanoids, Jasmonates, and Mimetics," Journal of Plant Growth Regulation, vol. 23, pp. 170-178, 2005.

Pan, X. et al. "Simultaneous Quantification of Major Phytohormones and Related Compounds in Crude Plant Extracts by Liquid Chromatography-Electrospray Tandem Mass Spectrometry," Phytochemistry, vol. 69, pp. 1773-1781, 2008.

Preston, C. et al. "Plant-Plant Signaling: Application of Trans- or Cis-Methyl Jasmonate Equivalent to Sagebrush Releases Does Not Elicit Direct Defenses in Native Tobacco," Journal of Chemical Ecology, vol. 30, No. 11, pp. 2193-2214, Nov. 2004.

Ryan, C. "Quantitative Determination of Soluble Cellular Proteins by Radial Diffusion in Agar Gels Containing Antibodies," Analytical Biochemistry, vol. 19, pp. 434-440, 1967.

Sheteawi, S., "Improving Growth and Yield of Salt-stressed Soybean by Exogenous Application of Jasmonic Acid and Ascobin," International Journal of Agriculture & Biology, vol. 9, No. 3, pp. 473-478, 2007.

Stanley, D. "Keeping Freshness in Fresh-Cut Produce," Agricultural Research, vol. 46, No. 2, pp. 12-14, 1998.

Stout, M. "Effect of Nitrogen Availability on Expression of Constitutive and Inducible Chemical Defenses in Tomato, *Lycopersicon esculentum*," Journal of Chemical Ecology, vol. 24, No. 6, pp. 946-963, 1998.

Susheng, G. "Senescence Processes in Plants," Journal of Plant Physiology, vol. 165, pp. 1970-1972, 2008.

Ueda, J. et al. "Isolation and Identification of a Senescence-promoting Substance from Wormwood (*Artemisia absinthium*L.)," Plant Physiology, vol. 66, pp. 246-249, 1980.

Wang, S. "Methyl Jasmonate Reduces Water Stress in Strawberry." Journal of Plant Growth Regulation, vol. 18, pp. 127-134, 1999.

Wijaya, C. et al. "Identification of Potent Odorants in Different Cultivars of Snake Fruit [*Salacca zalacca* (Gaert.) Voss] Using Gas Chromatography-Olfactometry," Journal of Agricultural and Food Chemistry, vol. 53, pp. 1637-1641, 2005.

* cited by examiner

METHODS OF REDUCING LEAF SENESCENCE USING METHYL DIHYDROJASMONATE

CROSS-REFERENCE TO RELATED APPLICATIONS

This application is a continuation-in-part of U.S. patent application Ser. No. 12/424,790, filed Apr. 16, 2009, now U.S. Pat. No. 8,013,226. That application claims priority to, and the benefit of, U.S. Provisional Patent Application No. 61/050,676, filed May 6, 2008. The contents of both of those applications are incorporated by reference in their entirety.

BACKGROUND OF THE INVENTION

1. Field of the Invention

Generally speaking, the invention relates to the field of plant biology, and more particularly, to methods for reducing leaf senescence using methyl dihydrojasmonate.

2. Description of Related Art

The jasmonates are a family of compounds related to jasmonic acid, 2-(3-oxo-2-(pent-2-enyl)cyclopentyl)acetic acid, the structure of which is shown below in Formula (I):

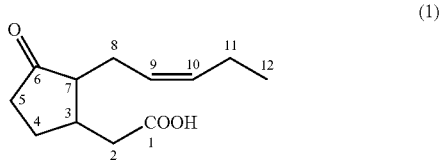

(1)

Jasmonates have been implicated in regulating a number of events in plant growth and development, as well as numerous types of plant responses to stressors. Osmotic stress or desiccation, touch, elicitation, wounding and pathogen and insect attack are all generally accompanied by increases in endogenous levels of jasmonates. Jasmonates are also widely used as flavoring and fragrance compounds because of their strong odor and taste characteristics.

In a number of studies, jasmonates have also been shown to promote leaf senescence, the process by which plant leaves age and ultimately die. Specifically, an extensive body of literature indicates that application of jasmonates, such as jasmonic acid (JA) and methyl jasmonate (MJ), promotes or accelerates leaf senescence in intact as well as excised plant leaves in such diverse plants as corn, rice, wheat, oat, barley, *arabidopsis*, sunflower, and zucchini (see, e.g., He et al., *Plant Physiology* 128 (2002), pp. 876-884; Ueda and Kato, *Plant Physiology* 66 (1980), pp. 246-249; Chou and Kao, *Plant Physiology* 99 (1992), pp. 1693-1694).

Aside from the purely biological implications of leaf senescence, the chlorosis (i.e., yellowing) and necrosis (i.e., tissue death) of senescing plant leaves can have commercial and practical implications. Senescing leaves may reduce success of crop establishment, survival, and performance. Senescing leaves may also be unattractive, and may detract significantly from both the perceived health and the commercial value of a plant or a crop of plants. The problem may be particularly acute where plants or portions thereof are grown and harvested primarily for their aesthetic properties, as is the case with roses. Reducing the levels of senescing leaves may also substantially improve the value of crops grown for food, particularly where the leaves of the plant are the edible portion (e.g., spinach).

SUMMARY OF THE INVENTION

One aspect of the invention relates to a method of reducing leaf senescence in a plant by treating the plant with an effective amount of methyl dihydrojasmonate. The methyl dihydrojasmonate may be in a variety of different forms, including emulsions, suspensions, powders, hydrates, solutions, granules, pastes, aerosols, and volatile formulations, and other additives and compounds may be included in the formulation. In one embodiment, the methyl dihydrojasmonate may be in the form of an aqueous solution, accompanied by a surfactant and an oil. The MDHJ may also be provided or co-administered with plant nutrients. After treatment, in some embodiments, the plant, or a portion thereof, may be harvested.

Another aspect of the invention relates to plants and portions thereof exhibiting reduced leaf senescence. The plants are prepared by a process comprising treating the plants with an effective amount of methyl dihydrojasmonate.

Yet other aspects of the invention relate to methods of reducing leaf senescence in plants. The methods comprise applying a liquid medium including methyl dihydrojasmonate to an exposed portion of an intact, established plant at least once until the exposed portion to which the liquid medium is applied is covered by or exposed to the liquid medium. The methyl dihydrojasmonate typically has a concentration of at least about 0.5 mM in the liquid medium. The methods also comprise evaluating the plant for evidence of leaf senescence.

Other aspects, features, and advantages of the invention will be set forth in the description that follows.

DETAILED DESCRIPTION

The present inventors have found that 9,10-dihydromethyl jasmonate, also called methyl dihydrojasmonate (MDHJ), the general structure of which is given below in Formula (2):

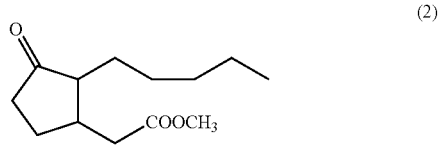 [SMILES: CCCCCC1C(=O)CCC1CC(=O)OC]

(2)

is surprisingly effective in reducing naturally occurring leaf senescence when administered to a plant in an effective amount. This effect is contrary to what would be expected from the literature on jasmonate effects in leaf senescence.

Plants to which MDHJ may be applied to reduce leaf senescence include, but are not limited to, angiosperms, gymnosperms, monocots, dicots, roses, tomatoes, crop plants, ornamental plants, turf plants, shrubs, trees, exotic plants, house plants, and native plants in cultivated or natural environments. MDHJ may also be applied to plants grown for food, particularly where the leaves are the edible or commercially desirable portion of the plant. MDHJ has been found to be particularly efficacious in roses, spinach, and corn.

The MDHJ may be applied alone or in a formulation comprising other elements, compounds, or substances. Some examples of other compounds that may be included in the formulation include wetting agents, adjuvants, emulsifiers, dispersants, spreaders, stickers, pastes, anchorage agents, fixatives, extenders, coating agents, buffering agents, plant nutrients, absorptive additives, and disintegrants. The formulation may also include acids, bases, or other compounds that adjust or maintain the final pH of the formulation in order to increase solubility of certain compounds in the formulation or for other reasons. Those of skill in the art will recognize that a single ingredient may perform multiple functions, and may thus be classified or grouped in different ways.

Particular examples of formulation ingredients include ionic, non-ionic, and zwitterionic surfactants, such as TRITON® X-100, TRITON® X-114, NP-40, SILWET, and sodium dodecyl sulfate; alcohols; synthetic or natural oils, such as castor oil, canola (rapeseed) oil, and soybean oil; soaps; and adjuvants derived from natural sources, such as lecithin, saponin, cocodiethanolamide, and extracts from yucca, coconut, and pine. Additionally, for example, citric acid may be used to acidify a formulation, and compounds such as dipotassium phosphate, calcium carbonate, and potassium silicate may be used to raise the pH.

In some embodiments, it may be beneficial to use ingredients that are high in compounds that play a role in the octadecanoic pathway. For example, canola oil is high in linoleic and linolenic acids, compounds that play a role in the octadecanoic pathway. Soaps of linoleic, linolenic, and cis-7,10, 13-hexadecatrienoic acids may also be desirable formulation ingredients in some embodiments.

An MDHJ formulation used in embodiments of the invention may also include fixative and extender compounds, in order to reduce volatility and evaporation of the active ingredient or ingredients, so as to increase exposure of the plant to the active ingredient. Exemplary fixatives include canola oil, castor oil, benzoyl benzoate, benzyl salicylate and synthetic musks, and sandalwood. Gums, waxes, and other carbohydrates, such as carnauba wax, carob gum, dextrins, dextrose, gellan gum, guar gum, paraffin wax, sorbitol, xanthan gum, polyvinylpyrrolidone, and glycerin, may also be used as fixatives.

Absorptive additives may also be included for extending the release and exposure time. Exemplary absorptive additives include, but are not limited to, silica gel; precipitated crystalline-free silica gel; amorphous, fumed, crystalline-free silica; amorphous, precipitated gel silica; silica hydrate; vitreous silica; silicic acid; and silicon dioxide.

Alone or in combination with other ingredients, the MDHJ may be delivered in the form of emulsions, suspensions, powders, hydrates, solutions, granules, pastes, aerosols, and volatile formulations. If MDHJ is delivered in the form of a solution, it may be in solution with any compatible solvent, including aqueous (water) solutions, alcohol (e.g., ethanol) solutions, or in combinations of solvents (e.g., water/ethanol.) In general, a "compatible solvent," as the term is used here, refers to any solvent in which MDHJ is at least slightly soluble and which is not phytotoxic in the amounts or concentrations used to apply the MDHJ.

Forms of MDHJ may be adapted for application to the plant's foliage, roots, stems, and flowers. Particularly advantageous forms include foliar sprays, root solutions, and pellet-based root preparations. As a root solution or preparation, jasmonates such as MDHJ may be formulated and applied to plants grown in soil, non-soil, artificial growing media, and/or hydroponic systems. In some embodiments, the MDHJ formulations may be combined with other active compounds that can be administered in the same fashion as the MDHJ formulation. Examples include fertilizers, seaweed, kelp, humic acid, and microbes. An MDHJ foliar spray may be combined with a foliar fertilizer, and a root solution may be combined with a fertilizer that is applied to the roots. Specific fertilizer and plant nutrient elements include, but are not limited to, nitrogen, potassium, phosphorus, calcium, magnesium, which may be compounded in any known manner so as to be absorbable by the plant. For example, plant nutrients may include monobasic potassium phosphate ($KH_2PO_4$) and magnesium sulfate ($MgSO_4$).

In addition to the above ingredients, formulations according to embodiments of the invention may also include preservatives. Suitable preservatives may include potassium sorbate, sodium benzoate, sulfites, sodium nitrite, EDTA, and calcium propionate, to name a few.

As was noted above, the MDHJ is applied in an "effective amount" to reduce leaf senescence. For purposes of this description, an effective amount of MDHJ is any amount of MDHJ that produces a noticeable decrease in leaf senescence as compared with untreated plants.

Effective amounts of MDHJ will vary from species to species and cultivar to cultivar, and will depend on the manner of application, the environmental conditions around the plant or plants, the form in which the MDHJ is administered, and the nature and type of additive compounds, if any, present in the formulation with the MDHJ. For example, if an MDHJ formulation is applied over a substantial portion of a plant's foliage, or is applied using a formulation that includes wetting agents, fixatives, and/or other additives intended to increase the level of exposure of the plant to the MDHJ, the formulation itself may contain a smaller amount or lower concentration of MDHJ than if an MDHJ formulation is applied over only a small portion of a plant's foliage, or without additives intended to increase the plant's exposure to the MDHJ. Similarly, if the MDHJ is administered in a form that tends to dwell on the plant's foliage, or in proximity to another part of the plant, then it may be administered in a lower concentration or amount.

As one example, an effective amount of MDHJ for reducing leaf senescence may comprise an aqueous solution with an MDHJ concentration in the range from about 0.15 mM to about 6 mM, inclusive. However, for some purposes, and in some species, concentrations up to or greater than 20 mM may be used. As those of skill in the art will realize, in general, MDHJ may be used in even higher concentrations for some applications, provided that the total dose of MDHJ that is absorbed by the plant is not phytotoxic. Similarly, lower concentrations may be adequate in some situations, for example, in an enclosed environment or greenhouse.

One example of an aqueous MDHJ foliar spray formulation is given below in Table 1:

TABLE 1

Exemplary aqueous MDHJ Foliar Spray Formulation.

| Ingredient | g/L | ml/L | % by weight | % by volume |
|---|---|---|---|---|
| Water | 993.411 | 993.411 | 99.3201% | 99.341% |
| Methyl Dihydrojasmonate (1.5 mM) | 0.339 | 0.339 | 0.0339% | 0.034% |
| Canola Oil | 4.600 | 5.000 | 0.4599% | 0.500% |
| Triton X-100 | 1.325 | 1.250 | 0.1325% | 0.125% |
| $KH_2PO_4$-2 mM | 0.272 | | 0.0272% | |
| $MgSO_4$-0.8 mM | 0.197 | | 0.0197% | |
| Citric Acid-0.347 mM | 0.067 | | 0.0067% | |
| Total | 1000.211 | 1000.000 | 1.000 | 1.000 |

In addition to liquid and aqueous preparations, MDHJ may be formulated for use in a slow-release application and provided in a granular- or pellet-based form, including fertilizer and/or pesticide components. MDHJ may be present in those formulations in weight/weight ratios of MDHJ to other ingredients in the range of 0.008% to 0.8%, and in some cases an effective ratio could be greater than 1.0% or less than 0.008%. Other inert or nutritive ingredients included in the pellets or granules can include binding agents and polymers, such as polysaccharides and polyvinylpyrrolidone, at 5-95%, a surfactant at 0.001-10%, and other absorptive ingredients, such as acrylamide and acrylamide polymers.

Formulations including MDHJ may be applied once or repeatedly, depending on the circumstances and the type of formulation, to treat a plant. For example, MDHJ formulations according to embodiments of the invention may be applied to the roots, foliage or some other part of a plant once or, alternatively, two or more times at defined intervals of time, such as every 2-14 days, every 30 days, or 1-2 times per month. The intervals at which the MDHJ is applied may vary. A plant may be treated with MDHJ whether or not it has senescing leaves at the time of treatment. Additionally, plants may be treated with MDHJ for purposes of reducing leaf senescence whether they are healthy or not. (For example, work by the present inventors has also shown that MDHJ is effective in reducing biotic attack and disease in plants; see, for example, U.S. Patent Application Publication No. 2009/0082453, the contents of which are incorporated by reference herein in their entirety. Therefore, a plant may be treated with MDHJ for multiple reasons.)

Among other factors, the environmental conditions around the plant or plants may influence the manner in which the MDHJ is applied or its frequency. For example, if the plants are field-grown or otherwise exposed to the elements, rain showers, excessive wind gusts, or other environmental factors shortly after an application, it may be desirable to reapply it. Under some circumstances, a more dilute formulation or solution may be used if repeated applications are to be performed.

Optionally, in at least some embodiments, a plant treated with MDHJ, or a portion thereof, may be harvested some time after the plant is treated with MDHJ. Harvesting may occur shortly after (e.g., several days after) treatment, or it may occur after sustained, relatively long-term treatment with MDHJ (e.g., several weeks or several months of treatment at regular intervals).

Treatment with MDHJ may reduce the levels of chlorosis and necrosis seen in plant leaves, and/or it may reduce the total number of senescing leaves, thus potentially improving the appearance of the plant and, consequently, its perceived health and/or commercial value.

EXAMPLES

The following examples serve to illustrate the efficacy of MDHJ in reducing leaf senescence. Unless otherwise noted, in the following examples, the MDHJ was obtained from Bedoukian Research, Inc. (Danbury, Conn., United States; product no. 398E). As supplied, the MDHJ solution was specified as having a minimum purity of 92.5%, of which 25-40% was the "epi" or "cis" isomer of MDHJ, shown as Formula (3) below:

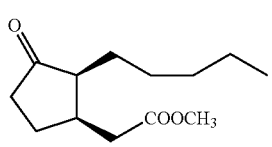

(3)

Unless otherwise noted, percentages, for example, percentages of additional or inert formulation ingredients, are given as percentages by volume.

Example 1

Foliar MDHJ Treatment Reduces Senescence in Miniature Roses

Potted miniature PARADE® roses were evaluated for the effect on leaf senescence of foliar spray treatment with an MDHJ formulation. One group of four plants acted as an untreated control group and did not receive any foliar spray. Another group of four plants was sprayed with a formulation comprising 1.5 mM MDHJ, 0.5% TRITON® X-100, and 0.125% canola oil. The treated plants were sprayed on six occasions, on days 1, 3, 12, 29, 31, and 58, by spraying foliage to the point of drip. The number of leaflets exhibiting senescence was analyzed 65 days after the first treatment. Senescence was indicated by chlorosis and necrosis affecting greater than 50% of an individual leaflet.

The results of Example 1 are shown in Table 2. Specifically, MDHJ treatment reduced leaf senescence normally associated with the end of the growing season. Sixty-five days after treatment, MDHJ-treated roses showed no senescing leaves, while untreated roses exhibited leaf senescence in up to 9.4% of their leaflets.

TABLE 2

Results of Example 1.

| | Plant | % Leaflets exhibiting senescence |
|---|---|---|
| Untreated Control | 1 | 8.2% |
| | 2 | 9.4% |
| | 3 | 8.2% |
| | 4 | 0.0% |
| MDHJ-Treated Plants | 1 | 0.0% |
| | 2 | 0.0% |
| | 3 | 0.0% |
| | 4 | 0.0% |

Example 2

Foliar MDHJ Treatment Reduces Senescence in Yellow Dwarf Rose

Potted Yellow Dwarf roses were grouped into one of four groups, and each of the groups received one treatment. The four groups are set forth in Table 3 below. One group was an untreated control (UTC), while the other three groups were treated with aqueous solutions of MDHJ that differed only in the concentration of MDHJ. There were three plants in each group. Before the trial began, naturally senescing leaves were visible on all plants; these were removed at the time that the trial began. The rose leaves received one foliar spray treatment by applying spray until the point of drip. Evaluation for leaf senescence, without any additional treatment, occurred on days 3, 7, 10, 14, and 31 by counting the number of leaves on each plant exhibiting senescence. Senescence was indicated by chlorosis and necrosis affecting greater than 50% of an individual leaf. After each evaluation, senescing leaves were removed.

TABLE 3

Treatment Groups for Example 2.

| Treatment Group | Formulation |
|---|---|
| 1 | Untreated Control Group |
| 2 | 1.5 mM MDHJ + 0.125% TRITON ® X-100 + 0.5% Canola Oil |
| 3 | 3.0 mM MDHJ + 0.125% TRITON ® X-100 + 0.5% Canola Oil |
| 4 | 6.0 mM MDHJ + 0.125% TRITON ® X-100 + 0.5% Canola Oil |

The results of Example 2 are shown in Table 4 below. In general, MDHJ treatment reduced the rate of naturally senescing leaves of Yellow Dwarf Rose compared to the untreated control group. In Table 4 below, treatment groups indicated by the same letter did not significantly differ (P=0.5, Student=Newman-Keuls).

TABLE 4

Results of Example 2.

| Treatment Group | Day 3 Mean No. Leaves | | Day 7 Mean No. Leaves | | Day 10 Mean No. Leaves | | Day 14 Mean No. Leaves | | Day 31 Mean No. Leaves | |
|---|---|---|---|---|---|---|---|---|---|---|
| 1 | 28 | a | 2 | a | 7 | a | 13 | a | 28 | a |
| 2 | 27 | a | 1 | b | 5 | ab | 13 | a | 27 | a |
| 3 | 25 | a | 1 | b | 4 | b | 12 | a | 25 | ab |
| 4 | 23 | a | 2 | a | 5 | ab | 12 | a | 23 | b |

Example 3

MDHJ Treatment Reduces Senescence in Spinach

Greenhouse-grown spinach seedlings, cultivar 'Merlo Nero,' were divided into two groups, with eight plants per group. One group was left untreated, while the other group was treated with 0.5 mM MDHJ in 0.1% ethanol by spraying leaves until the point of drip. Treatments occurred on days 1, 4 and 8 of the experiment. On day 6, senescence was noted on some leaves, defined by chlorosis and/or necrosis. Senescence began at the leaf tip and spread towards the petiole. On day 8, the number of plants exhibiting senescence was counted. All leaves from each plant were then harvested and combined for each treatment. The total number of senescing leaves were counted and taken as a percentage of the total number of leaves per treatment. Senescence was indicated by chlorosis and necrosis affecting greater than 50% of an individual leaf.

In the untreated spinach group, 87.5% of the plants exhibited signs of senescence compared to 37.5% in the treated group. In the untreated group, 34.6% of the leaves exhibited senescence. In the treated group, 8.6% of the leaves showed senescence. The full results of Example 3 are set forth below in Table 5 below.

TABLE 5

Results of Example 3.

| | Untreated | Treated |
|---|---|---|
| % of Leaves Exhibiting Senescence | 34.6% | 8.6% |
| % of Plants Exhibiting Senescence | 87.5% | 37.5% |
| Number of Senescent Leaves | 36 | 8 |
| Total Number of Leaves | 104 | 93 |
| Number of Plants Exhibiting Chlorosis or Necrosis | 7 | 3 |
| Total Number of Plants | 8 | 8 |

Example 4

MDHJ Reduces Leaf Senescence in Corn

Seeds of corn ('Kandy Korn', extra sweet) were planted in 2-inch pots. Seedlings were germinated under 16-hour day/8-hour night greenhouse conditions. Plants were placed outdoors and received 5-6 hours of natural, direct light. Eighteen days after planting, seedlings received one of two treatments.

Treatment 1 (n=11): Foliar spray with water—control
Treatment 2 (n=12): Foliar spray of 1 mM MDHJ in water.

Plant leaves from both treatments were sprayed until the point of drip and allowed to air dry before being randomly combined into the same growing tray (to provide plants from both treatments with identical growing conditions). Because MDHJ has relatively low solubility in water, the MDHJ treatment solution/suspension was shaken vigorously before the MDHJ was applied to the plants.

Plants were observed and visible leaf senescence recorded 6 days after the single treatment. Plants were scored according to presence or absence of senescence on any leaf of the plant. Table 6 contains the results. As shown in Table 6, 64% of control plants (Treatment 1) exhibited visibly senescing leaves as indicated by yellowing of the leaf, whereas only 27% of the plants that received foliar MDHJ treatment (Treatment 2) exhibited yellowing. Of the plants with senescing leaves, only one leaf per plant had senescence (10%) in the Treatment 2 group. In Treatment 1, three of the seven (or 43%) plants showed yellow leaves on two leaves per plant. The remaining four plants showed senescence on one leaf (Table 1).

In addition to the presence or absence of senescence, the severity of senescence, as indicated by the average percent leaf area that is yellow, was greater in plants in Treatment 2 than Treatment 1. Senescing leaves in Treatment 2 plants showed a mean of 15% yellow per leaf. In contrast, senescing leaves in the Treatment 1 group had a mean of 43% of the leaf area exhibiting senescing.

TABLE 6

Results of Example 4.

| | Treatment 1 (n = 11) | Treatment 2 (n = 12) |
|---|---|---|
| % of plants with senescing leaves | 64% | 27% |
| % of plants with one senescent leaf | 36% | 25% |
| % of plants with two senescent leaves | 27% | 0% |

All references cited above are hereby incorporated by reference in their entireties.

While the invention has been described with respect to certain embodiments and examples, the description is intended to be illustrative, rather than limiting. Modifications and changes may be made within the scope of the invention, which is defined by the appended claims.

What is claimed is:

1. A method of reducing leaf senescence, comprising:
applying a liquid medium including methyl dihydrojasmonate to an exposed portion of an intact, established plant at least once until the exposed portion to which the liquid medium is applied is covered by or exposed to the liquid medium, the methyl dihydrojasmonate having a concentration of at least 0.5 mM in the liquid medium; and
evaluating the plant for evidence indicative of leaf senescence, including one or both of chlorosis or necrosis.

2. The method of claim 1, wherein the methyl dihydrojasmonate has a concentration in the liquid medium of 0.5 to 6.0 mM.

3. The method of claim 2, wherein the methyl dihydrojasmonate has a concentration in the liquid medium of at least 1.0 mM.

4. The method of claim 2, wherein the liquid medium further includes a surfactant and an oil.

5. The method of claim 2, wherein the liquid medium further includes an alcohol or a surfactant.

6. The method of claim 1, wherein the applying comprises applying the liquid medium to the foliage of the plant once with the methyl dihydrojasmonate in a concentration of at least 1.0 mM in the liquid medium.

7. The method of claim 1, wherein the plant is a corn, spinach, or rose plant.

8. A method of reducing leaf senescence in roses, comprising:
applying a liquid medium including methyl dihydrojasmonate to an exposed portion of an intact, established rose plant at least once until the foliage to which the liquid medium is applied is covered by or exposed to the liquid medium, the methyl dihydrojasmonate having a concentration of 0.5 mM to 6.0 mM in the liquid medium; and
evaluating the rose plant for evidence indicative of leaf senescence, including one or both of chlorosis or necrosis.

9. The method of claim 8, wherein the liquid medium further includes a surfactant.

10. The method of claim 9, wherein the surfactant is selected from the group consisting of TRITON® X-100, TRITON® X-114, NP-40, SILWET, and sodium dodecyl sulfate.

11. The method of claim 8, wherein the liquid medium further includes an alcohol.

12. The method of claim 8, wherein the liquid medium further includes an oil.

13. The method of claim 8, wherein the liquid medium further comprises a fixative selected from the group consisting of canola oil, castor oil, benzoyl benzoate, benzyl salicylate, synthetic musk, sandalwood, carnauba wax, carob gum, dextrin, dextrose, gellan gum, guar gum, paraffin wax, sorbitol, xanthan gum, polyvinylpyrrolidone, and glycerin.

14. The method of claim 8, wherein the liquid medium further comprises an absorptive additive selected from the group consisting of silica gel; precipitated crystalline-free silica gel; amorphous, fumed, crystalline-free silica; amorphous, precipitated gel silica; silica hydrate; vitreous silica; silicic acid; and silicon dioxide.

15. The method of claim 8, wherein the liquid medium further comprises a surfactant and an oil.

16. The method of claim 8, wherein the liquid medium further comprises one or more plant nutrients.

17. The method of claim 8, wherein the liquid medium comprises one or more of ingredients selected from the group consisting of lecithin, saponin, and cocodiethanolamide.

18. A method of reducing leaf senescence, comprising:
applying a liquid medium including methyl dihydrojasmonate to an exposed portion of an intact, established plant at least once until the exposed portion to which the liquid medium is applied is covered by or exposed to the liquid medium, the methyl dihydrojasmonate having a concentration of about 0.5 mM to 6.0 mM in the liquid medium; and
evaluating the plant for evidence indicative of leaf senescence, including one or both of chlorosis or necrosis.

19. A method of producing a plant or plant portion with reduced leaf senescence, comprising:
applying a liquid medium including methyl dihydrojasmonate to an exposed portion of an intact, established plant at least once until the exposed portion to which the liquid medium is applied is covered by or exposed to the liquid medium, the methyl dihydrojasmonate having a concentration of about 0.5 mM to 10.0 mM in the liquid medium;
evaluating the plant for evidence indicative of leaf senescence; and
harvesting the plant, or a portion of the plant, at a defined time after said applying.

* * * * *